(12) United States Patent
Jung et al.

(10) Patent No.: US 11,851,412 B2
(45) Date of Patent: *Dec. 26, 2023

(54) DIAMINE COMPOUND, METHOD OF PREPARING THE SAME, AND COMPOSITION CONTAINING THE SAME

(71) Applicants: SK Innovation Co., Ltd., Seoul (KR); SK ie technology Co., Ltd., Seoul (KR)

(72) Inventors: Min Seon Jung, Daejeon (KR); Hyo Shin Kwak, Daejeon (KR); Joo Hyun Lee, Daejeon (KR)

(73) Assignees: SK Innovation Co., Ltd., Seoul (KR); SK ie technology Co., Ltd., Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/463,873

(22) Filed: Sep. 1, 2021

(65) Prior Publication Data

US 2022/0073480 A1  Mar. 10, 2022

(30) Foreign Application Priority Data

Sep. 4, 2020 (KR) .................. 10-2020-0112996

(51) Int. Cl.
*C07D 263/57* (2006.01)

(52) U.S. Cl.
CPC .................. *C07D 263/57* (2013.01)

(58) Field of Classification Search
CPC .................................... C07D 263/57
See application file for complete search history.

(56) References Cited

U.S. PATENT DOCUMENTS

| 2004/0102435 A1 | 5/2004 | Barlaam et al. |
| 2011/0081428 A1 | 4/2011 | Lithgow et al. |

FOREIGN PATENT DOCUMENTS

| CN | 110204719 A | 9/2019 |
| CN | 110776657 A | 2/2020 |
| CN | 111019345 A | 4/2020 |
| JP | 2004524289 A | 8/2004 |
| KR | 1020100039792 A | 4/2010 |

OTHER PUBLICATIONS

Choi et al., "Soluble polyimides from unsymmetrical diamine containing benzimidazole ring and trifluoromethyl pendent group", Polymer, 2008, pp. 2644-2649, vol. 49, Elsevier.

*Primary Examiner* — Shawquia Jackson
(74) *Attorney, Agent, or Firm* — THE WEBB LAW FIRM

(57) ABSTRACT

The present invention relates to a diamine compound, a method of preparing the same, and a composition containing the same. The diamine compound of the present invention may be very usefully used as a monomer used to produce a polyimide film having excellent heat resistance and improved transparency and coefficient of thermal expansion.

6 Claims, No Drawings

DIAMINE COMPOUND, METHOD OF PREPARING THE SAME, AND COMPOSITION CONTAINING THE SAME

CROSS-REFERENCE TO RELATED APPLICATION

This application claims priority to Korean Patent Application No. 10-2020-0112996 filed Sep. 4, 2020, the disclosure of which is hereby incorporated by reference in its entirety.

BACKGROUND OF THE INVENTION

Field of the Invention

The following disclosure relates to a novel diamine compound, a method of preparing the same, and a composition containing the same, and more particularly, to a diamine compound that is a monomer usefully used in production of a polyimide film, a method of preparing the same, and a composition containing the same.

Description of Related Art

Polyimide has attracted attention as a material that has high heat resistance and is light and flexible. In such a polyimide field, aromatic polyimide has attracted attention as a resin having excellent thermal dimensional stability. A polyimide film, which is a molded article formed of aromatic polyimide having a rigid and linear chemical structure, has been widely used in a field requiring high thermal dimensional stability (a low coefficient of linear thermal expansion), such as a base film of a flexible substrate or an interlayer insulating film of a semiconductor. However, since the aromatic polyimide having a low coefficient of linear thermal expansion is strongly colored by intermolecular conjugation and a charge transfer interaction in molecules or between molecules, it is difficult to apply the aromatic polyimide to an optical use. In addition, since the polyimide has a significantly strong intermolecular force, the polyimide is insufficient in processability.

Meanwhile, a flexible device is manufactured by applying a polyimide precursor composition onto a transport substrate, curing the polyimide precursor composition to form a film, completing a device through a subsequent process such as deposition of a thin film transistor (TFT) and an organic film, and detaching the completed device from the transport substrate. It is required for such a flexible device obtained by being subjected to a high-temperature process to have heat resistance at a high temperature. In particular, in a case where a thin film transistor process in which low temperature polysilicon (LIPS) is used is performed, a process temperature may reach 500° C. Therefore, the polyimide film to be formed on the transport substrate is required not to be thermally decomposed by hydrolysis and to have high heat resistance even during the high-temperature process. In addition, it is required for the polyimide film to secure transparency after processing as well as storage stability.

Therefore, in order to manufacture a flexible device, there is a need for novel polyimide having high heat resistance and preventing hydrolysis, thereby implementing excellent chemical resistance and storage stability and improving optical and mechanical properties.

Physical properties of polyimide are derived from a monomer used for preparing the same. Thus, it is required to develop a novel monomer in order to prepare polyimide having further improved physical properties.

SUMMARY OF THE INVENTION

An embodiment of the present invention is directed to providing a novel diamine compound significantly useful as a monomer used to provide a polyimide film having excellent heat resistance and significantly improved physical properties such as transparency, a yellow index, and a Young's modulus, and a method of preparing the same.

Another embodiment of the present invention is directed to providing a composition containing the novel diamine compound of the present invention.

An object of the present invention is to provide a diamine compound useful as a monomer of a polyimide precursor used to produce a polyimide film having improved physical properties.

In one general aspect, there is provided a novel diamine compound represented by the following Chemical Formula 1,

[Chemical Formula 1]

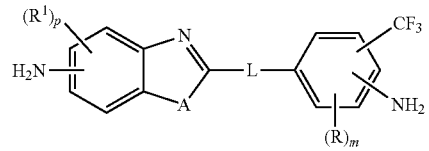

in Chemical Formula 1,

A is O or S;

R and $R^1$ are each independently halogen, C1-C10 alkyl, halo C1-C10 alkyl, C1-C10 alkoxy, or C6-C12 aryl;

L is a single bond, C1-C10 alkylene, C6-C12 arylene,

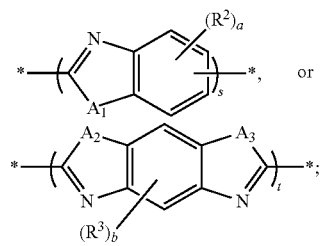

$A_1$ to $A_3$ are each independently O or S;

$R^2$ and $R^3$ are each independently halogen, C1-C10 alkyl, halo C1-C10 alkyl, C1-C10 alkoxy, or C6-C12 aryl;

s and t are each independently an integer of 1 to 5;

a is an integer of 0 to 3;

b is an integer of 0 to 2;

m is an integer of 0 to 3; and p is an integer of 0 to 3.

In Chemical Formula 1,

A may be O;

m may be an integer of 0 or 1;

R and $R^1$ may be each independently halogen, C1-C10 alkyl, or halo C1-C10 alkyl;

L may be a single bond, C1-C10 alkylene, C6-C12 arylene, each of $A_1$ to $A_3$ may be O;
$R^2$ and $R^3$ may be each independently halogen, C1-C10 alkyl, or halo C1-C10 alkyl;
s and t may be each independently an integer of 1 to 3;
a may be an integer of 0 or 1;
b may be an integer of 0 or 1; and
p may be an integer of 0 or 1.

In Chemical Formula 1, each of A and $A_1$ to $A_3$ may be O; L may be a single bond, C1-C10 alkylene, or C6-C12 arylene; and each of m and p may be 0.

Chemical Formula 1 may be represented by the following Chemical Formula 2,

[Chemical Formula 2]

in Chemical Formula 2,
A is O or S;
$R^{11}$ and $R^{12}$ are each independently halogen, C1-C10 alkyl, halo C1-C10 alkyl, C1-C10 alkoxy, or C6-C12 aryl; and
n and m are each independently an integer of 0 to 2.

In order to prepare polyimide having further improved physical properties, Specifically, in Chemical Formula 2, A may be O; $R^{11}$ and $R^{12}$ may be each independently halogen, C1-C10 alkyl, or halo C1-C10 alkyl; and n and m may be each independently an integer of 0 or 1, and more Specifically, $R^{11}$ and $R^{12}$ may be each independently halogen, C1-C5 alkyl, or halo C1-C5 alkyl; and n and m may be each independently an integer of 0 or 1.

The novel diamine compound may be selected from the following compounds, but is not limited thereto.

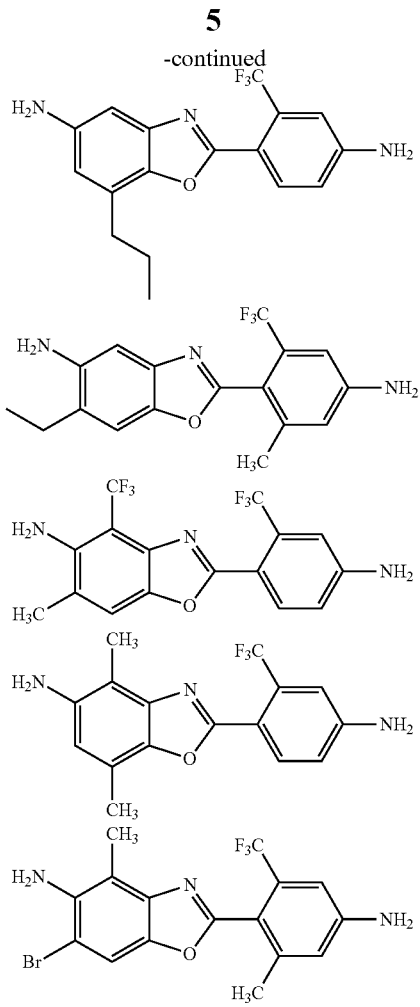

In another general aspect, there is provided a method of preparing a diamine compound.

The method of preparing a diamine compound includes preparing a diamine compound represented by the following Chemical Formula 1 by subjecting a compound represented by the following Chemical Formula 11 to a reduction reaction,

[Chemical Formula 1]

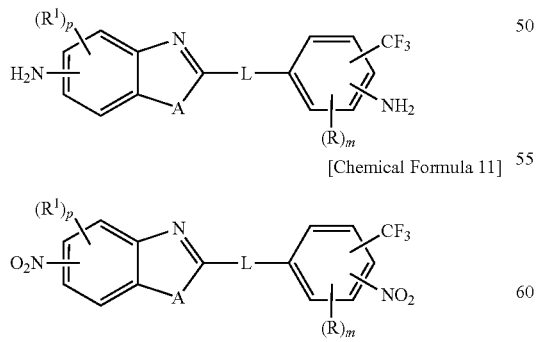

[Chemical Formula 11]

in Chemical Formulas 1 and 11,

A is O or S;

R and $R^1$ are each independently halogen, C1-C10 alkyl, halo C1-C10 alkyl, C1-C10 alkoxy, or C6-C12 aryl;

p is an integer of 0 to 3;

m is an integer of 0 to 3;

L is a single bond, C1-C10 alkylene, C6-C12 arylene,

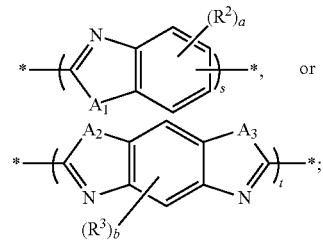

$A_1$ to $A_3$ are each independently O or S;

$R^2$ and $R^3$ are each independently halogen, C1-C10 alkyl, halo C1-C10 alkyl, C1-C10 alkoxy, or C6-C12 aryl;

s and t are each independently an integer of 1 to 5;

a is an integer of 0 to 3; and b is an integer of 0 to 2.

The reduction reaction may be performed with hydrogen and one or two or more selected from, Pd/C, Raney-nickel, Rh/C, Pt/C, and Ru/C.

In the method, the diamine compound may be prepared by: preparing a compound represented by the following Chemical Formula 14 by reacting a compound represented by the following Chemical Formula 12 and a compound represented by the following Chemical Formula 13; and preparing the compound represented by Chemical Formula 11 by subjecting the compound represented by Chemical Formula 14 to a dehydration reaction,

[Chemical Formula 12]

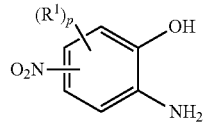

[Chemical Formula 13]

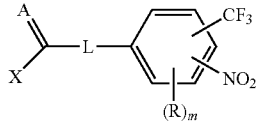

[Chemical Formula 14]

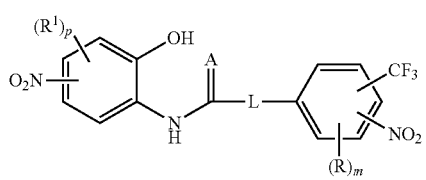

in Chemical Formulas 12 to 14,

A is O or S;

R and $R^1$ are each independently halogen, C1-C10 alkyl, halo C1-C10 alkyl, C1-C10 alkoxy, or C6-C12 aryl;

p is an integer of 0 to 3;

m is an integer of 0 to 3;

L is a single bond, C1-C10 alkylene, C6-C12 arylene,

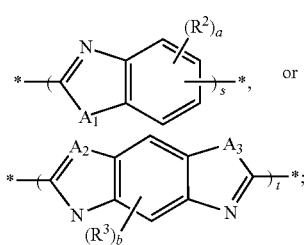

A₁ to A₃ are each independently O or S;

R² and R³ are each independently halogen, C1-C10 alkyl, halo C1-C10 alkyl, C1-C10 alkoxy, or C6-C12 aryl;

s and t are each independently an integer of 1 to 5;

a is an integer of 0 to 3;

b is an integer of 0 to 2; and x is halogen.

In still another general aspect, there is provided a composition containing the diamine compound.

The diamine compound may be contained in an amount of 1 to 30 wt % with respect to a total weight of the composition.

Other features and aspects will be apparent from the following detailed description, the drawings, and the claims.

DESCRIPTION OF THE INVENTION

Unless otherwise defined, all the technical terms and scientific terms used herein have the same meanings as commonly understood by those skilled in the art to which the present invention pertains. The terms used in the description of the present invention are merely used to effectively describe a specific exemplary embodiment, but are not intended to limit the present invention.

Unless the context clearly indicates otherwise, the singular forms used in the specification may be intended to include the plural forms.

In addition, units used in the present specification without special mention are based on weight, and as an example, a unit of % or a ratio refers to wt % or a weight ratio. Unless otherwise defined, wt % refers to wt % of any one component in a composition with respect to a total weight of the composition.

In addition, a numerical range used in the present specification includes upper and lower limits and all values within these limits, increments logically derived from a form and span of a defined range, all double limited values, and all possible combinations of the upper and lower limits in the numerical range defined in different forms. Unless otherwise particularly defined in the present specification, all values out of the numerical range that may occur due to the rounding off of the experimental errors or values also fall within the defined numerical ranges.

In the present specification, the expression "comprise(s)" is intended to be an open-ended transitional phrase having an equivalent meaning to "include(s)," "contain(s)," "have (has)," and "is (are) characterized by," and does not exclude elements, materials, or steps, all of which are not further recited herein.

In the present specification, the term "polyimide precursor solution" refers to a composition used for preparing polyimide, and specifically, the polyimide precursor may have an equivalent meaning to polyamic acid. In addition, the polyimide precursor solution may also be used as a composition used for preparing polyamideimide.

In the present specification, the term "polyimide film" refers to a molded article formed of polyimide derived from the polyimide precursor solution and may have an equivalent meaning to polyimide.

In the present specification, the term "halogen" refers to a fluorine (F), chloride (Cl), bromine (Br), or iodine (I) atom.

In the present specification, the term "alkyl" refers to an organic radical derived from an aliphatic hydrocarbon by removal of one hydrogen atom and includes both linear and branched forms.

In the present specification, the term "alkoxy" is represented by "*—O-alkyl", and the alkyl is the same as defined above.

In the present specification, the term "haloalkyl" refers to the alkyl in which one hydrogen is substituted with halogen.

In the present specification, the term "aryl" refers to an organic radical derived from an aromatic hydrocarbon by removal of one hydrogen, includes a monocyclic or fused ring system having suitably 4 to 7 ring atoms, and Specifically 5 or 6 ring atoms in each ring, and even includes a form in which a plurality of aryls are linked by a single bond. Examples of the aryl include, but are not limited to, phenyl, naphthyl, biphenyl, and terphenyl.

The present invention provides a novel diamine compound, and the diamine compound of the present invention is represented by the following Chemical Formula 1.

[Chemical Formula 1]

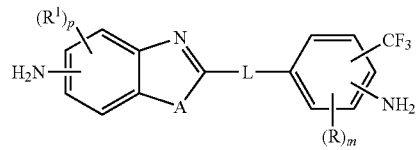

In Chemical Formula 1,

R and R¹ are each independently halogen, C1-C10 alkyl, halo C1-C10 alkyl, C1-C10 alkoxy, or C6-C12 aryl;

m is an integer of 0 to 3;

L is a single bond, C1-C10 alkylene, C6-C12 arylene,

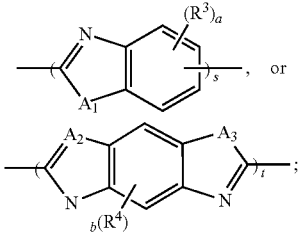

A₁ to A₃ are each independently O or S;

R² and R³ are each independently halogen, C1-C10 alkyl, halo C1-C10 alkyl, C1-C10 alkoxy, or C6-C12 aryl;

s and t are each independently an integer of 1 to 5;

a is an integer of 0 to 3;

b is an integer of 0 to 2; and p is an integer of 0 to 3.

The diamine compound of the present invention has a specific linking group

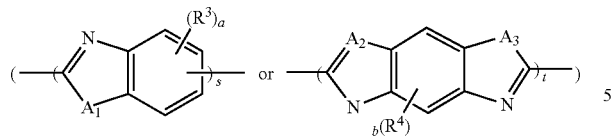

or a specific functional group

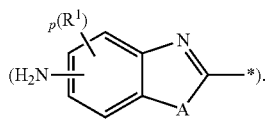

Therefore, a polyimide film produced using the diamine compound as a monomer has improved physical properties.

Specifically, in the diamine compound of the present invention, benzoxazole, benzothiazole, benzobisoxazole, or benzobisthiazole is introduced as a linking group, or benzoxazole or benzothiazole having an amino group as a substituent is introduced. Therefore, when the diamine compound is used as a monomer, it is possible to produce a polyimide film excellent in a coefficient of thermal expansion, transparency, a yellow index, and heat resistance.

In order to prepare polyimide having further improved physical properties, in Chemical Formula 1 according to an exemplary embodiment of the present invention, R and $R^1$ may be each independently halogen, C1-C10 alkyl, or halo C1-C10 alkyl;

m may be an integer of 0 or 1;

L may be a single bond, C1-C10 alkylene, C6-C12 arylene,

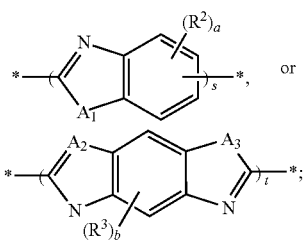

each of $A_1$ to $A_3$ may be O;

$R^2$ and $R^3$ may be each independently halogen, C1-C10 alkyl, or halo C1-C10 alkyl;

s and t may be each independently an integer of 1 to 3;

a may be an integer of 0 or 1;

b may be an integer of 0 or 1; and p may be an integer of 0 or 1.

specifically, in Chemical Formula 1 according to an exemplary embodiment of the present invention, each of A and $A_1$ to $A_3$ may be O;

L may be a single bond, C1-C10 alkylene, or C6-C12 arylene; and each of m and p may be 0.

In detail, R may be C1-C5 alkyl or halo C1-C5 alkyl; m may be an integer of 0 or 1; L may be a single bond, C1-C5 alkylene, C6-C10 arylene,

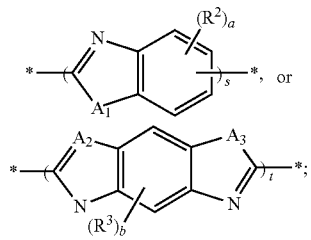

each of $A_1$ to $A_3$ may be O; $R^2$ and $R^3$ may be each independently C1-C5 alkyl or halo C1-C5 alkyl; s and t may be each independently an integer of 1 or 2; a may be an integer of 0 or 1; b may be an integer of 0 or 1; $R^1$ may be C1-C5 alkyl or halo C1-C5 alkyl; and p may be an integer of 0 or 1.

Still more specifically, m may be 0; L may be a single bond, C1-C3 alkylene, C6-C8 arylene,

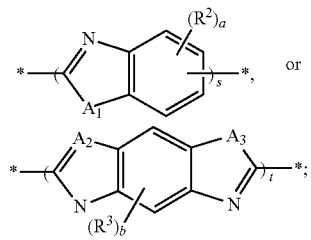

each of $A_1$ to $A_3$ may be O; s and t may be each independently an integer of 1 or 2; each of a and b may be 0; and p may be 0.

more specifically, Chemical Formula 1 according to an exemplary embodiment of the present invention may be represented by the following Chemical Formula 2.

[Chemical Formula 2]

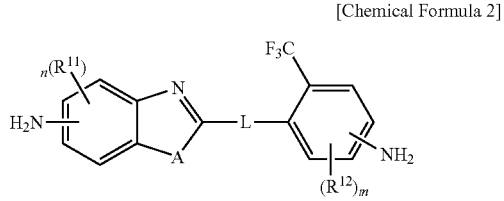

In Chemical Formula 2,

A is O or S;

$R^{11}$ and $R^{12}$ are each independently halogen, C1-C10 alkyl, halo C1-C10 alkyl, C1-C10 alkoxy, or C6-C12 aryl; and n and m are each independently an integer of 0 to 2.

$CF_3$ is present at a specific position of the diamine compound represented by Chemical Formula 2 according to an exemplary embodiment of the present invention, such that the diamine compound may have a further improved transmittance and transparency.

In addition, the diamine compound represented by Chemical Formula 2 according to an exemplary embodiment of the present invention does not have problems of warpage, peeling, and fracture even being subjected to a heat treatment, and may have a uniform transmittance and transparency.

Therefore, specifically, in Chemical Formula 2, A may be O; $R^{11}$ and $R^{12}$ may be each independently halogen, C1-C10 alkyl, or halo C1-C10 alkyl; and n and m may be each independently an integer of 0 or 1.

More specifically, in Chemical Formula 2 according to an exemplary embodiment of the present invention, A may be O; $R^{11}$ and $R^{12}$ may be each independently halogen, C1-C5 alkyl, or halo C1-C5 alkyl; and n and m may be each independently an integer of 0 or 1.

Specifically, the novel diamine compound according to an exemplary embodiment of the present invention may be selected from the following compounds, but is not limited thereto.

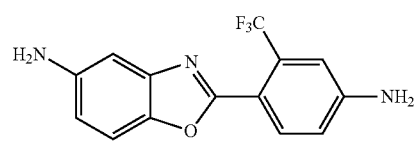
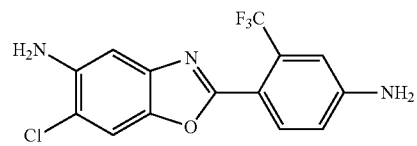
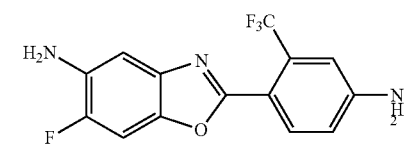
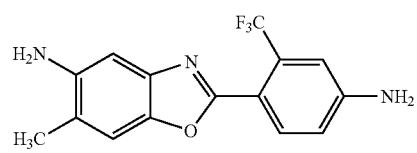
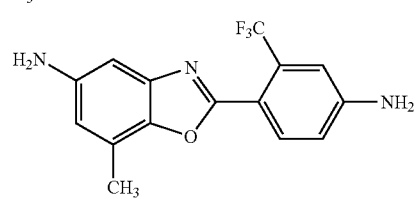
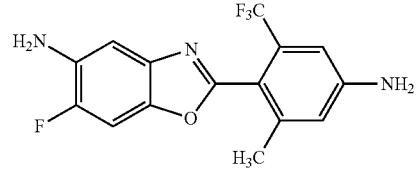
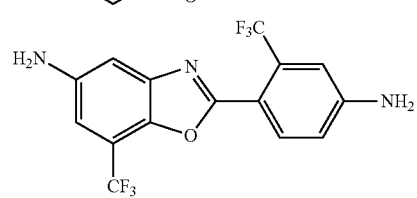

-continued

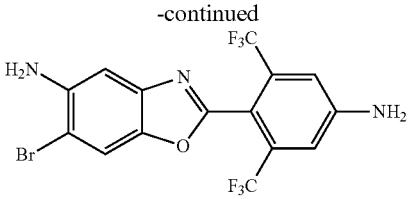
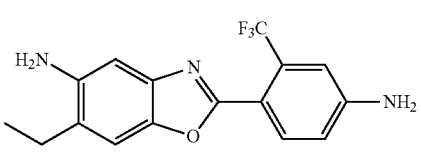
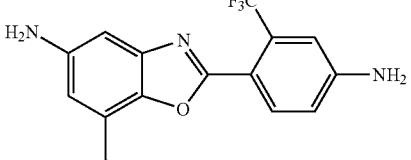
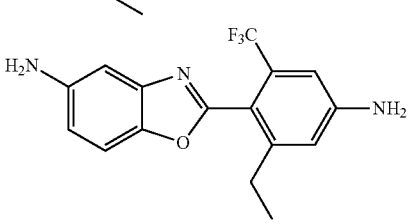
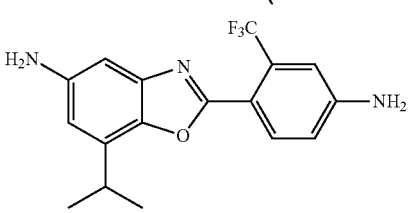
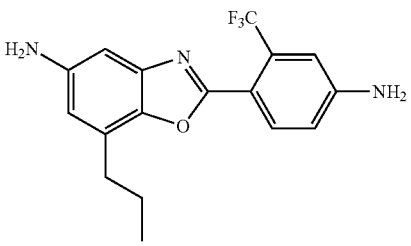
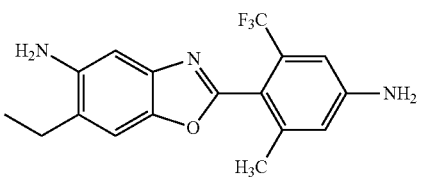
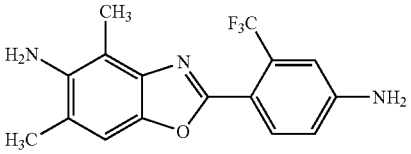
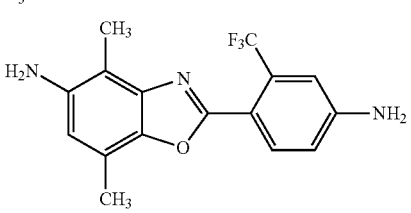

-continued

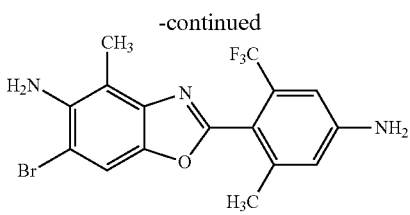

In addition, the present invention provides a method of preparing a diamine compound. The method of preparing a diamine compound of the present invention includes preparing a diamine compound represented by the following Chemical Formula 1 by subjecting a compound represented by the following Chemical Formula 11 to a reduction reaction.

[Chemical Formula 1]

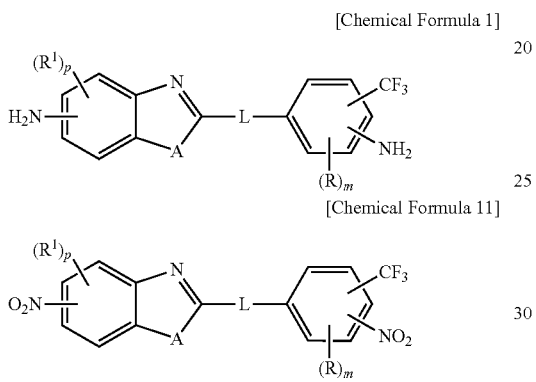

[Chemical Formula 11]

In Chemical Formulas 1 and 11,
A is O or S;
$R^1$ is halogen, C1-C10 alkyl, halo C1-C10 alkyl, C1-C10 alkoxy, or C6-C12 aryl;
p is an integer of 0 to 3;
R is halogen, C1-C10 alkyl, halo C1-C10 alkyl, C1-C10 alkoxy, or C6-C12 aryl;
m is an integer of 0 to 3;
L is a single bond, C1-C10 alkylene, C6-C12 arylene,

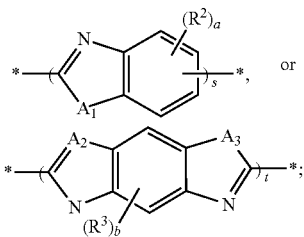

$A_1$ to $A_3$ are each independently O or S;
$R^2$ and $R^3$ are each independently halogen, C1-C10 alkyl, halo C1-C10 alkyl, C1-C10 alkoxy, or C6-C12 aryl;
s and t are each independently an integer of 1 to 5;
a is an integer of 0 to 3; and
b is an integer of 0 to 2.

The reduction reaction according to an exemplary embodiment of the present invention may be performed with hydrogen and one or two or more selected from Pd/C, Raney-nickel, Rh/C, Pt/C, and Ru/C.

The reduction reaction may be performed at room temperature (5° C. to 35° C.) for 1 to 10 hours and specifically at 10° C. to 35° C. for 2 to 8 hours.

In the method of preparing a diamine compound, the diamine compound may be prepared by: preparing a compound represented by the following Chemical Formula 14 by reacting a compound represented by the following Chemical Formula 12 and a compound represented by the following Chemical Formula 13; and preparing the compound represented by Chemical Formula 11 by subjecting the compound represented by Chemical Formula 14 to a dehydration reaction.

[Chemical Formula 12]

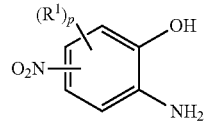

[Chemical Formula 13]

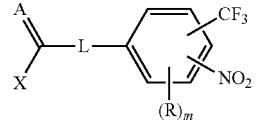

[Chemical Formula 14]

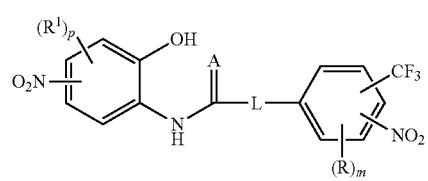

In Chemical Formulas 12 to 14,
A is O or S;
R and $R^1$ are each independently halogen, C1-C10 alkyl, halo C1-C10 alkyl, C1-C10 alkoxy, or C6-C12 aryl;
p is an integer of 0 to 3;
m is an integer of 0 to 3;
L is a single bond, C1-C10 alkylene, C6-C12 arylene,

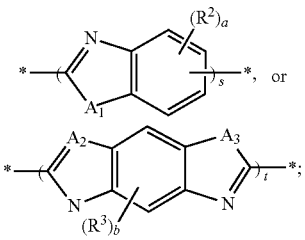

$A_1$ to $A_3$ are each independently O or S;
$R^2$ and $R^3$ are each independently halogen, C1-C10 alkyl, halo C1-C10 alkyl, C1-C10 alkoxy, or C6-C12 aryl;
s and t are each independently an integer of 1 to 5;
a is an integer of 0 to 3;
b is an integer of 0 to 2; and
X is halogen.

The dehydration reaction according to an exemplary embodiment of the present invention may be performed using a dehydrating agent, and a specific dehydrating agent is used. Any dehydrating agent may be used as long as it is used in the dehydration reaction, and specific examples thereof may include one or two or more selected from acetic acid, acetic anhydride, and methylbenzenesulfonic acid.

The dehydration reaction may be performed at room temperature (5° C. to 35° C.) for 1 to 10 hours and specifically at 10° C. to 35° C. for 2 to 8 hours.

The present invention provides a polyimide precursor prepared using the novel diamine compound as a monomer.

Specifically, the polyimide precursor according to an exemplary embodiment of the present invention has a structural unit derived from the novel diamine compound represented by Chemical Formula 1 having a specific structure and a structural unit derived from an acid dianhydride compound.

In the polyimide precursor of the present invention, a benzothiazolyl group or a benzoxazolyl group is included, or benzoxazole, benzothiazole, benzobisoxazole, or benzobisthiazole is introduced as a linking group, such that the polyimide precursor has linearity and rigidity, and a polyimide film produced using the polyimide precursor has significantly improved optical and mechanical properties such as a coefficient of thermal expansion, high heat resistance, chemical resistance, and transparency.

The polyimide precursor according to an exemplary embodiment of the present invention may further have a structural unit derived from a diamine compound other than the structural unit derived from the diamine compound represented by Chemical Formula 1. Examples of the diamine compound to be further included may include 4,4'-diaminodiphenyl propane, 4,4'-diaminodiphenyl methane, 4,4'-diaminodiphenyl sulfide, 3,3'-diaminodiphenyl sulfone, 4,4'-diaminodiphenyl sulfone, 4,4'-oxydianiline, 3,3'-oxydianiline, 3,4'-oxydianiline, 4,4'-diaminodiphenyl diethylsilane, 4,4'-diaminodiphenyl silane, 4,4'-diaminodiphenyl ethylphosphine oxide, 4,4'-diaminodiphenyl N-methylamine, 4,4'-diaminodiphenyl N-phenylamine, 1,4-diaminobenzene(p-phenylenediamine), bis{4-(4-aminophenoxy)phenyl}sulfone, bis{4-(3-aminophenoxy)phenyl}sulfone, 4,4'-bis(4-aminophenoxy)biphenyl, 4,4'-bis(3-aminophenoxy)biphenyl, 1,3-bis(3-aminophenoxy)benzene, 1,3-bis(4-aminophenoxy)benzene, 1,3-bis(3-aminophenoxy)benzene, 3,3'-diaminobenzophenone, 4,4'-diaminobenzophenone, and 2,2-bis(4-aminophenoxyphenyl)propane, and these diamine compounds may be used alone or in combination thereof, but the present invention is not limited thereto.

Specifically, the polyimide precursor according to an exemplary embodiment of the present invention may further have a structural unit derived from a diamine compound represented by the following Chemical Formula 1-1.

[Chemical Formula 1-1]

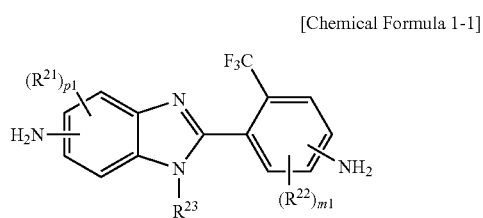

In Chemical Formula 1-1, $R^{21}$ and $R^{22}$ are each independently halogen, (C1-C10) alkyl, halo(C1-C10)alkyl, (C1-C10)alkoxy, or (C6-C12) aryl;

$R^{23}$ is hydrogen, (C1-C10)alkyl, halo(C1-C10)alkyl, (C1-C10)alkoxy, or (C6-C12)aryl; and each of p1 and m1 is an integer of 0 to 3.

The polyimide precursor according to an exemplary embodiment of the present invention may further have the structural unit derived from the diamine compound represented by Chemical Formula 1-1, such that a polyimide film having excellent optical and mechanical properties may be produced, and a polyimide film whose physical properties are controlled may be implemented.

Specifically, in Chemical Formula 1-1 according to an exemplary embodiment of the present invention, $R^{21}$ and $R^{22}$ may be each independently halogen, (C1-C10)alkyl, or halo(C1-C10)alkyl; $R^{23}$ may be hydrogen or (C1-C10)alkyl; and each of p1 and m1 may be an integer of 0 or 1, more specifically, $R^{21}$ and $R^{22}$ may be each independently halogen, (C1-C5)alkyl, or halo(C1-C5)alkyl; $R^{23}$ may be hydrogen or (C1-C5)alkyl; and each of p1 and m1 may be an integer of 0 or 1, and still more specifically, each of p1 and m1 may be 0.

The polyimide precursor according to an exemplary embodiment of the present invention may further have a structural unit derived from a diamine compound represented by the following Chemical Formula 1-2.

[Chemical Formula 1-2]

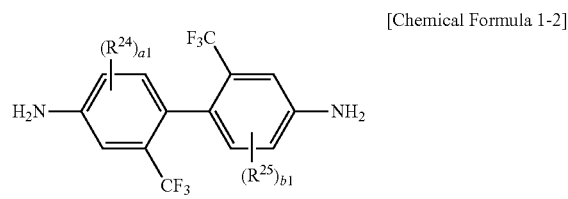

In Chemical Formula 1-2, $R^{24}$ and $R^{25}$ are each independently halogen, (C1-C10) alkyl, halo(C1-C10)alkyl, (C1-C10)alkoxy, or (C6-C12) aryl; and a and b are each independently an integer of 0 to 3.

Specifically, in Chemical Formula 1-2, $R^{24}$ and $R^{25}$ may be each independently halogen, (C1-C10)alkyl, or halo(C1-C10)alkyl; and a and b may be each independently an integer of 0 or 1, and more specifically, each of a and b may be 0.

As the acid dianhydride according to an exemplary embodiment of the present invention, any compound may be used as long as it has an acid dianhydride functional group, and a specific example of the acid dianhydride may include tetracarboxylic dianhydride. The tetracarboxylic dianhydride may be a compound selected from (C8-C36) aromatic tetracarboxylic dianhydride, (C6-C36) aliphatic tetracarboxylic dianhydride, and (C6-C36) alicyclic tetracarboxylic dianhydride. In order to have an excellent yellow index even at a high-temperature region, the tetracarboxylic dianhydride may be specifically (C8-C36) aromatic tetracarboxylic dianhydride. The number of carbon atoms in the tetracarboxylic dianhydride according to an exemplary embodiment of the present invention includes the number of carbon atoms contained in a carboxyl group. Specifically, specific examples of the tetracarboxylic dianhydride according to an exemplary embodiment of the present invention may include 4,4'-(hexafluoroisopropylidene)diphthalic anhydride, 5-(2,5-dioxotetrahydro-3-furanyl)-3-methyl-cyclohexene-1,2-dicarboxylic anhydride, pyromellitic dianhydride, 1,2,3,4-benzenetetracarboxylic dianhydride, 3,3',4,4'-benzophenonetetracarboxylic dianhydride, 2,2',3,3'-benzophenonetetracarboxylic dianhydride, 3,3',4,4'-biphenyltetracarboxylic dianhydride, 3,3',4,4'-diphenylsulfonetetracarboxylic dianhydride, 2,2',3,3'-biphenyltetracarboxylic dianhydride, methylene-4,4'-diphthalic dianhydride, 1,1-ethylidene-4,4'-diphthalic dianhydride, 2,2-propylidene-4,4'-diphthalic dianhydride, 1,2-ethylene-4,4'-diphthalic dianhydride, 1,3-trimethylene-4,4'-diphthalic dianhydride, 1,4-tetramethylene-4,4'-diphthalic dianhydride, 1,5-pentamethylene-4,4'-diphthalic dianhydride, 4,4'-oxydiphthalic dianhydride, p-phenylenebis(trimellitate anhydride), thio-4,4'-diphthalic dianhydride, sulfonyl-4,4'-diphthalic dianhydride, 1,3-bis(3,4-dicarboxyphenyl)benzene dianhydride, 1,3-bis(3,4-dicarboxyphenoxy)benzene dianhydride, 1,4-bis(3,4-dicarboxyphenoxy)benzene dianhydride, 1,3-bis[2-(3,4-dicarboxyphenyl)-2-propyl]benzene dianhydride, 1,4-bis[2-(3,4-dicarboxyphenyl)-2-propyl]benzene dianhydride, bis[3-(3,4-dicarboxyphenoxy)phenyl]methane dianhydride, bis[4-(3,4-dicarboxyphenoxy)phenyl]methane dianhydride, 2,2-bis[3-(3,4-dicarboxyphenoxy)phenyl]propane dianhydride, 2,2-bis[4-(3,4-dicarboxyphenoxy)phenyl]propane dianhydride, bis(3,4-dicarboxyphenoxy)dimethylsilane dianhydride, 1,3-bis(3,4-dicarboxyphenyl)-1,1,3,3-tetramethyldisiloxane dianhydride, 2,3,6,7-naphthalenetetracarboxylic dianhydride, 1,4,5,8-naphthalenetetracarboxylic dianhydride, 1,2,5,6-naphthalenetetracarboxylic dianhydride, 3,4,9,10-perylenetetracarboxylic dianhydride, 2,3,6,7-anthracenetetracarboxylic dianhydride, and 1,2,7,8-phenanthrenetetracarboxylic dianhydride. Specifically, examples of the (C6-C50) aliphatic tetracarboxylic dianhydride may include ethylenetetracarboxylic dianhydride and 1,2,3,4-butanetetracarboxylic dianhydride, and examples of the (C6-C36) alicyclic tetracarboxylic dianhydride may include 1,2,3,4-cyclobutanetetracarboxylic dianhydride, cyclopentanetetracarboxylic dianhydride, cyclohexane-1,2,3,4-tetracarboxylic dianhydride, cyclohexane-1,2,4,5-tetracarboxylic dianhydride, 3,3',4,4'-bicyclohexyltetracarboxylic dianhydride, carbonyl-4,4'-bis(cyclohexane-1,2-dicarboxylic) dianhydride, methylene-4,4'-bis(cyclohexane-1,2-dicarboxylic) dianhydride, 1,2-ethylene-4,4'-bis(cyclohexane-1,2-dicarboxylic) dianhydride, 1,1-ethylidene-4,4'-bis(cyclohexane-1,2-dicarboxylic) dianhydride, 2,2-propylidene-4,4'-bis(cyclohexane-1,2-dicarboxylic) dianhydride, oxy-4,4'-bis(cyclohexane-1,2-dicarboxylic) dianhydride, thio-4,4'-bis(cyclohexane-1,2-dicarboxylic) dianhydride, sulfonyl-4,4'-bis(cyclohexane-1,2-dicarboxylic) dianhydride, bicyclo[2,2,2]oct-7-ene-2,3,5,6-tetracarboxylic dianhydride, 4-(2,5-dioxotetrahydrofuran-3-yl)-1,2,3,4-tetrahydronaphthalene-1,2-dicarboxylic anhydride, and ethylene glycol-bis-(3,4-dicarboxylic anhydride phenyl)ether.

In order to implement excellent chemical resistance and yellow index, more specifically, the acid dianhydride may be an acid dianhydride represented by the following Chemical Formula 1-3 in a preferred combination with the diamine compound of the present invention.

[Chemical Formula 1-3]

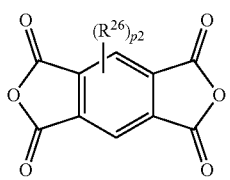

In Chemical Formula 1-3,
$R^{26}$ is (C1-C10)alkyl or halo(C1-C10)alkyl; and
p2 is an integer of 0 to 2.

Specifically, in Chemical Formula 1-3 according to an exemplary embodiment of the present invention, $R^{26}$ may be (C1-C5)alkyl or halo(C1-C5)alkyl; and p2 may be an integer of 0 or 1, and more specifically, $R^{26}$ may be (C1-C5)alkyl or halo(C1-C5)alkyl; and p2 may be 0.

Specifically, the polyimide precursor according to an exemplary embodiment of the present invention may further have a structural unit derived from an acid dianhydride represented by the following Chemical Formula 1-4.

[Chemical Formula 1-4]

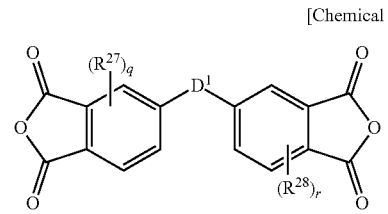

In Chemical Formula 1-4,
$D^1$ is (C1-C10)alkylene substituted or unsubstituted with halo(C1-C10)alkyl;
$R^{27}$ and $R^{28}$ are each independently (C1-C10)alkyl or halo(C1-C10)alkyl; and
q and r are each independently an integer of 0 to 2.

Specifically, in Chemical Formula 1-4 according to an exemplary embodiment of the present invention, $D^1$ may be (C1-C5)alkylene substituted or unsubstituted with halo(C1-C5)alkyl; $R^{27}$ and $R^{28}$ may be each independently (C1-C5) alkyl; and q and r may be each independently an integer of 0 or 1, more specifically, $D^1$ may be (C1-C3)alkylene substituted or unsubstituted with halo(C1-C3)alkyl; $R^{27}$ and $R^{28}$ may be each independently halo(C1-C3)alkyl; and q and r may be each independently an integer of 0 or 1, and still more specifically, $D^1$ may be (C1-C3)alkylene substituted or unsubstituted with halo(C1-C3)alkyl; $R^{27}$ and $R^{28}$ may be each independently (C1-C3)alkyl; and each of q and r may be 0.

The polyimide precursor according to an exemplary embodiment of the present invention may have a repeating unit represented by the following Chemical Formula 1-5.

[Chemical Formula 1-5]

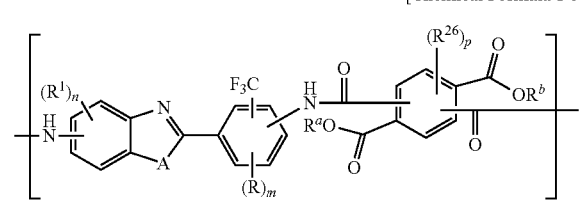

In Chemical Formula 1-5,
A is O or S;
$R^1$ and R are each independently halogen, C1-C10 alkyl, halo C1-C10 alkyl, C1-C10 alkoxy, or C6-C12 aryl;
$R^{26}$ is (C1-C10)alkyl or halo(C1-C10)alkyl;
$R^a$ and $R^b$ are each independently hydrogen or (C1-C10) alkyl;
m and n are each independently an integer of 0 to 3; and
p is an integer of 0 to 2.

Specifically, in Chemical Formula 1-5 according to an exemplary embodiment of the present invention, A may be O; $R^1$ and R may be each independently halogen, (C1-C10) alkyl, or halo(C1-C10)alkyl; $R^{26}$ may be (C1-C10)alkyl or halo(C1-C10)alkyl; $R^a$ and $R^b$ may be each independently hydrogen or (C1-C10)alkyl; m and n may be each independently an integer of 0 or 1; and p may be an integer of 0 or 1, more specifically, A may be O; $R^1$ and R may be each independently halogen, (C1-C5)alkyl, or halo(C1-C5)alkyl; $R^{26}$ may be (C1-C5)alkyl or halo(C1-C5)alkyl; $R^a$ and $R^b$ may be each independently hydrogen or (C1-C5)alkyl; m and n may be each independently an integer of 0 or 1; and p may be an integer of 0 or 1, and still more specifically, A may be O; and each of m, n, and p may be 0.

The repeating unit represented by Chemical Formula 1-5 may be included in the polyimide precursor according to an exemplary embodiment of the present invention in an amount of 10 to 100 mol %, specifically 30 to 100 mol %, more specifically 40 to 95 mol %, and still more specifically 50 to 80 mol %.

Specifically, the polyimide precursor according to an exemplary embodiment of the present invention may further have a repeating unit represented by the following Chemical Formula 1-6.

[Chemical Formula 1-6]

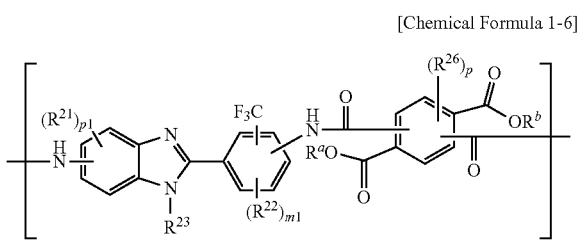

(C1-C10)alkyl; $R^a$ and $R^b$ may be each independently hydrogen or C1-C10 alkyl; p1 and m1 may be each independently an integer of 0 to 3; and p may be an integer of 0 to 2, more specifically, $R^{21}$ and $R^{22}$ may be each independently halogen, (C1-C5)alkyl, or halo(C1-C5)alkyl; $R^{23}$ may be hydrogen, (C1-C5)alkyl, or halo(C1-C5)alkyl; $R^{26}$ may be (C1-C5)alkyl or halo(C1-C5)alkyl; $R^a$ and $R^b$ may be each independently hydrogen or C1-C5 alkyl; p1 and m1 may be each independently an integer of 0 or 1; and p may be an integer of 0 or 1, and still more specifically, $R^{26}$ may be (C1-C5)alkyl; $R^a$ and $R^b$ may be each independently hydrogen or C1-C5 alkyl; and each of p1, m1, and p may be 0.

The repeating unit represented by Chemical Formula 1-6 according to an exemplary embodiment of the present invention may be included in the polyimide precursor in an amount of 10 to 90 mol %, specifically 30 to 80 mol %, more specifically 40 to 70 mol %, and still more specifically 50 to 60 mol %, with respect to a total mol % of the polyimide precursor.

Specifically, the polyimide precursor according to an exemplary embodiment of the present invention may further have repeating units represented by the following Chemical Formulas 1-7 and 1-8.

[Chemical Formula 1-7]

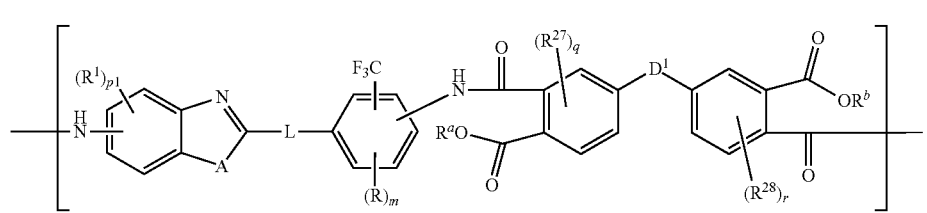

[Chemical Formula 1-8]

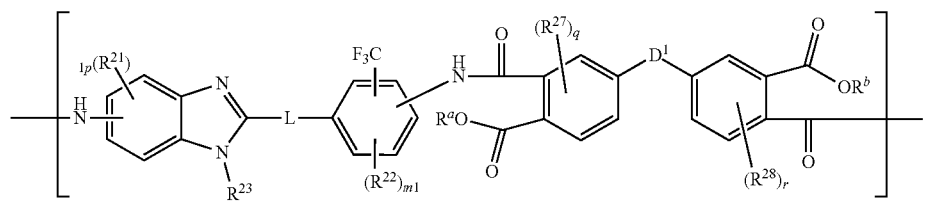

In Chemical Formula 1-6, $R^{21}$ and $R^{22}$ are each independently halogen, (C1-C10)alkyl, halo(C1-C10)alkyl, (C1-C10)alkoxy, or (C6-C12)aryl;

$R^{23}$ is hydrogen, (C1-C10)alkyl, halo(C1-C10)alkyl, (C1-C10)alkoxy, or (C6-C12)aryl;

$R^{26}$ is (C1-C10)alkyl or halo(C1-C10)alkyl;

$R^a$ and $R^b$ are each independently hydrogen or C1-C10 alkyl;

p1 and m1 are each independently an integer of 0 to 3; and p is an integer of 0 to 2.

Specifically, in Chemical Formula 1-6 according to an exemplary embodiment of the present invention, $R^{21}$ and $R^{22}$ may be each independently halogen, (C1-C10)alkyl, or halo(C1-C10)alkyl; $R^{23}$ may be hydrogen, (C1-C10)alkyl, or halo(C1-C10)alkyl; $R^{26}$ may be (C1-C10)alkyl or halo In Chemical Formulas 1-7 and 1-8, A is O or S;

$D^1$ is (C1-C10)alkylene substituted or unsubstituted with halo(C1-C10)alkyl;

R, $R^1$, $R^{21}$, and $R^{22}$ are each independently halogen, C1-C10 alkyl, halo C1-C10 alkyl, C1-C10 alkoxy, or C6-C12 aryl;

$R^{23}$ is hydrogen, (C1-C10)alkyl, halo(C1-C10)alkyl, (C1-C10)alkoxy, or (C6-C12)aryl;

$R^{27}$ and $R^{28}$ are each independently (C1-C10)alkyl or halo(C1-C10)alkyl;

$R^a$ and $R^b$ are each independently hydrogen or C1-C10 alkyl;

m and n are each independently an integer of 0 to 3;

q and r are each independently an integer of 0 to 2; and p1 and m1 are each independently an integer of 0 to 3.

Specifically, in Chemical Formulas 1-7 and 1-8, A may be O; $D^1$ may be (C1-C10)alkylene substituted or unsubstituted with halo(C1-C5)alkyl; R, $R^1$, $R^{21}$, and $R^{22}$ may be each independently halogen, C1-C10 alkyl, or halo C1-C10 alkyl; $R^{23}$ may be hydrogen or (C1-C10)alkyl; $R^{27}$ and $R^{28}$ may be each independently (C1-C5)alkyl or halo(C1-C5)alkyl; $R^a$ and $R^b$ may be each independently hydrogen or (C1-C5) alkyl; and m, n, q, r, s, and t may be each independently an integer of 0 or 1.

The repeating unit represented by Chemical Formula 1-7 according to an exemplary embodiment of the present invention may be included in the polyimide precursor in an amount of 10 to 90 mol %, specifically 30 to 80 mol %, more specifically 40 to 70 mol %, and still more specifically 50 to 60 mol %, with respect to the total mol % of the polyimide precursor.

The repeating unit represented by Chemical Formula 1-8 according to an exemplary embodiment of the present invention may be included in the polyimide precursor in an amount of 10 to 50 mol %, specifically 30 to 50 mol %, and more specifically 40 to mol %, with respect to the total mol % of the polyimide precursor.

The polyimide precursor according to an exemplary embodiment of the present invention may essentially have the repeating unit represented by Chemical Formula 1-5 and may further have the repeating unit represented by Chemical Formula 1-6. Specifically, the polyimide precursor may essentially have the repeating unit represented by Chemical Formula 1-5 and may further have the repeating unit represented by Chemical Formula 1-7. More specifically, the polyimide precursor may essentially have the repeating unit represented by Chemical Formula 1-5 and may further have the repeating unit represented by Chemical Formula 1-6 and the repeating unit represented by Chemical Formula 1-7. Still more specifically, the polyimide precursor may essentially have the repeating unit represented by Chemical Formula 1-5, and may further have the repeating unit represented by Chemical Formula 1-6, the repeating unit represented by Chemical Formula 1-7, and the repeating unit represented by Chemical Formula 1-8.

In addition, the present invention provides a composition containing the diamine compound according to an exemplary embodiment of the present invention. The composition according to an exemplary embodiment of the present invention may be a polyimide precursor composition containing a polyimide precursor and a solvent.

The diamine compound may be contained in the composition containing the diamine compound of the present invention in an amount of 1 to 30 wt % with respect to a total weight of the composition.

The polyimide precursor composition of the present invention contains the polyimide precursor of the present invention, such that it is possible to implement a polyimide film having significantly improved optical and mechanical properties.

The polyimide precursor composition of the present invention may provide a polyimide film having high transparency and heat resistance and excellent thermal dimensional stability because a stress of a substrate does not increase even after performing a heat treatment at a high temperature. In particular, it is possible to provide a polyimide film having excellent transparency and a low coefficient of linear thermal expansion.

The polyimide precursor composition according to an exemplary embodiment of the present invention may be one or a mixture of two or more selected from ketones such as γ-butyrolactone, 1,3-dimethyl-2-imidazolidinone, methyl ethyl ketone, cyclohexanone, cyclopentanone, and 4-hydroxy-4-methyl-2-pentanone; aromatic hydrocarbons such as toluene, xylene, and tetramethylbenzene; glycol ethers (cellosolves) such as ethylene glycol monoethyl ether, ethylene glycol monomethyl ether, ethylene glycol monobutyl ether, diethylene glycol monoethyl ether, diethylene glycol monomethyl ether, diethylene glycol monobutyl ether, propylene glycol monomethyl ether, propylene glycol monoethyl ether, dipropylene glycol diethyl ether, and triethylene glycol monoethyl ether; acetates such as ethyl acetate, butyl acetate, ethylene glycol monoethyl ether acetate, ethylene glycol monobutyl ether acetate, diethylene glycol monoethyl ether acetate, and dipropylene glycol monomethyl ether acetate; alcohols such as methanol, ethanol, propanol, ethylene glycol, propylene glycol, and carbitol; and amides such as N,N-dimethylpropionamide (DMPA), N,N-diethylpropionamide (DEPA), N,N-dimethylacetamide (DMAc), N,N-diethylacetamide, N,N-dimethylformamide (DMF), N,N-diethylformamide (DEF), N-methylpyrrolidone (NMP), N-ethylpyrrolidone (NEP), and N,N-dimethylmethoxy acetamide.

As an example, the organic solvent may be one or a mixture of two or more selected from the amides described above.

As an example, a boiling point of the organic solvent may be 300° C. or lower. As a specific example, the organic solvent may be N,N-diethylformamide (DEF), N,N-diethylacetamide (DEAc), N-ethylpyrrolidone (NEP), N,N-dimethylpropionamide (DMPA), N,N-diethylpropionamide (DEPA), or a combination thereof.

In the polyimide precursor composition according to an exemplary embodiment of the present invention, a solid content of the polyimide precursor having the repeating unit represented by Chemical Formula 1-5 may be 10 to 13 wt % with respect to a total weight of the composition.

Specifically, a viscosity of the polyimide precursor composition according to an exemplary embodiment of the present invention may be 2,000 to 10,000 cps. The viscosity may be, specifically, 8,000 cps or less, and more specifically, 7,000 cps or less. When the viscosity is in the above range, the process efficiency may be excellent due to excellent defoamation efficiency when processing a polyimide film. As a result, a more uniform surface may be implemented, which is preferable. In this case, the viscosity means a value measured by placing a sample at room temperature (25° C.) using a Brookfield RVDV-III viscometer spindle No. 52 and stabilizing the sample for 2 minutes at the time when a torque value reaches 80%.

A polyimide precursor solution according to an exemplary embodiment of the present invention may be prepared by polymerizing the diamine compound according to an exemplary embodiment of the present invention and an acid dianhydride in the presence of a solvent. A molar ratio of the diamine compound according to an exemplary embodiment of the present invention to the acid dianhydride may be 2:1 to 1:2, 1.5:1 to 1:1.5, or 1.1:1 to 1:1.1.

The polymerization of the diamine compound according to an exemplary embodiment of the present invention and the acid dianhydride may be performed at 70° C. or lower, 10° C. to 70° C., or 20° C. to 30° C.

In addition, a polyimide film may be produced by imidizing the polyimide precursor of the present invention or the polyimide precursor solution of the present invention.

As an example, the imidization may be performed by a chemical imidization method or a thermal imidization method.

The imidization according to the present invention may be performed by a thermal imidization method. In a case where the imidization is performed by heat at a high temperature by the thermal imidization method, uniform mechanical properties may be imparted to the entire film, which is preferable. Specifically, the polyimide film according to the present invention may be produced by a production method including applying and coating the polyimide precursor solution described above onto a substrate and performing a heat treatment.

The heat treatment according to an exemplary embodiment of the present invention may be performed at 500° C. or lower.

Specifically, the heat treatment may include a first heat treatment step performed at 100° C. or lower, a second heat treatment step performed at higher than 100° C. and 300° C. or lower, and a third heat treatment step performed at higher than 300° C. and 500° C. or lower, but the present invention is not limited thereto.

As the substrate according to an exemplary embodiment of the present invention, a glass substrate, a metal substrate, or a plastic substrate may be used without particular limitation. Among them, it is preferable to use a glass substrate that has excellent thermal and chemical stability during processes for imidizing and curing the polyimide precursor solution, and may be easily separated without damage to the polyimide film formed after curing even without an additional release agent.

The application and coating method according to an exemplary embodiment of the present invention is not particularly limited, and as a specific example, one or more methods selected from a spin coating method, a dipping method, a spray method, a die coating method, a bar coating method, a roll coating method, a meniscus coating method, a flexo printing method, a screen printing method, a bead coating method, an air knife coating method, a reverse roll coating method, a blade coating method, a casting coating method, and a gravure coating method, may be used.

After the heat treatment step according to an exemplary embodiment of the present invention, a step of drying a film and a step of separating the film from the substrate may be further performed.

A molecular weight of the polyimide precursor having the repeating unit represented by Chemical Formula 1-5 according to an exemplary embodiment of the present invention is not particularly limited. However, as an example, when a weight average molecular weight of the polyimide precursor is in a range of 20,000 to 150,000 g/mol, more excellent physical properties may be obtained.

In addition, the polyimide precursor solution according to an exemplary embodiment of the present invention may further contain additives such as a leveling agent, a flame retardant, an adhesion improver, an inorganic particle, an antioxidant, a UV stabilizer, and a plasticizer.

The present invention provides a polyimide film produced using the polyimide precursor composition of the present invention. The polyimide film of the present invention has a repeating unit represented by the following Chemical Formula 1-9.

[Chemical Formula 1-9]

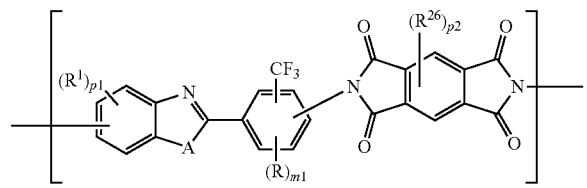

In Chemical Formula 1-9,
A is O or S;
$R^1$ and R are each independently halogen, (C1-C10)alkyl, halo(C1-C10)alkyl, (C1-C10)alkoxy, or (C6-C12)aryl;
$R^{26}$ is (C1-C10)alkyl or halo(C1-C10)alkyl;
p1 and m1 are each independently an integer of 0 to 2; and
p2 is an integer of 0 to 2.

Specifically, in Chemical Formula 1-9 according to an exemplary embodiment of the present invention, A may be O; $R^1$ and R may be each independently halogen, (C1-C10)alkyl, or halo(C1-C10)alkyl; $R^{26}$ may be (C1-C10)alkyl; p1 and m1 may be each independently an integer of 0 or 1; and p2 may be an integer of or 1, more specifically, A may be O; $R^1$ and R may be each independently halogen, (C1-C5)alkyl, or halo(C1-C5)alkyl; $R^{26}$ may be (C1-C5)alkyl; p1 and m1 may be each independently an integer of 0 or 1; and p2 may be an integer of 0 or 1, and still more specifically, A may be O; $R^1$ and R may be each independently halogen, (C1-C5)alkyl, or halo(C1-C5)alkyl; $R^{26}$ may be (C1-C5)alkyl; and each of p1, m1, and p2 may be 0.

Specifically, the polyimide film according to an exemplary embodiment of the present invention may further have a repeating unit represented by the following Chemical Formula 1-10.

[Chemical Formula 1-10]

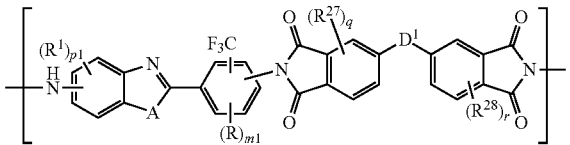

In Chemical Formula 1-10,
A is O or S;
$D^1$ is (C1-C10)alkylene substituted or unsubstituted with halo(C1-C10)alkyl;
$R^1$ and R are each independently halogen, C1-C10 alkyl, halo C1-C10 alkyl, C1-C10 alkoxy, or C6-C12 aryl;
$R^{27}$ and $R^{28}$ are each independently (C1-C10)alkyl or halo(C1-C10)alkyl;
p1 and m1 are each independently an integer of 0 to 3; and
q and r are each independently an integer of 0 to 2.

Specifically, in Chemical Formula 1-10, A may be O; $D^1$ may be (C1-C10)alkylene substituted or unsubstituted with halo(C1-C5)alkyl; $R^1$ and R may be each independently halogen, C1-C10 alkyl, or halo C1-C10 alkyl; and p1, m1, q, and r may be each independently an integer of 0 or 1.

More specifically, the polyimide film according to an exemplary embodiment of the present invention may further have a repeating unit represented by the following Chemical Formula 1-11.

[Chemical Formula 1-11]

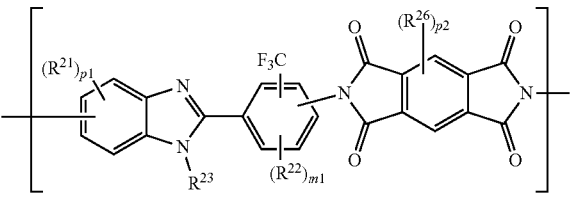

In Chemical Formula 1-11, $R^{21}$ and $R^{22}$ are each independently halogen, (C1-C10)alkyl, halo(C1-C10)alkyl, (C1-C10)alkoxy, or (C6-C12)aryl;

$R^{23}$ is hydrogen, halogen, (C1-C10)alkyl, halo(C1-C10)alkyl, (C1-C10)alkoxy, or (C6-C12)aryl;

$R^{26}$ is (C1-C10)alkyl or halo(C1-C10)alkyl;

each of p1 and m1 is an integer of 0 to 3; and p2 is an integer of 0 to 2.

Specifically, in Chemical Formula 1-11 according to an exemplary embodiment of the present invention, $R^{21}$ and $R^{22}$ may be each independently halogen, (C1-C10)alkyl, or halo(C1-C10)alkyl; $R^{23}$ may be hydrogen, (C1-C10)alkyl, or halo(C1-C10)alkyl; $R^{26}$ may be (C1-C10)alkyl or halo(C1-C10)alkyl; each of p1 and m1 may be an integer of 0 or 1; and p2 may be an integer of 0 or 1, more specifically, $R^{21}$ and $R^{22}$ may be each independently halogen, (C1-C5)alkyl, or halo(C1-C5)alkyl; $R^{23}$ may be hydrogen, (C1-C5)alkyl, or halo(C1-C5)alkyl; $R^{26}$ may be (C1-C5)alkyl or halo(C1-C5)alkyl; each of p1 and m1 may be an integer of 0 or 1; and p2 may be an integer of 0 or 1, and still more specifically, $R^{21}$ and $R^{22}$ may be each independently halogen, (C1-C10)alkyl, or halo(C1-C10)alkyl; $R^{23}$ may be hydrogen, (C1-C10)alkyl, or halo(C1-C10)alkyl; $R^{26}$ may be (C1-C10)alkyl or halo(C1-C10)alkyl; and each of p1, m1, and p2 may be 0.

Still more specifically, the polyimide film according to an exemplary embodiment of the present invention may further have a repeating unit represented by the following Chemical Formula 1-12.

[Chemical Formula 1-12]

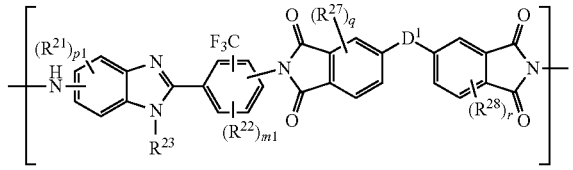

In Chemical Formula 1-12, $D^1$ is (C1-C10)alkylene substituted or unsubstituted with halo(C1-C10)alkyl;

$R^{21}$ and $R^{22}$ are each independently halogen, C1-C10 alkyl, halo C1-C10 alkyl, C1-C10 alkoxy, or C6-C12 aryl;

$R^{23}$ is hydrogen, (C1-C10)alkyl, halo(C1-C10)alkyl, (C1-C10)alkoxy, or (C6-C12)aryl;

$R^{27}$ and $R^{28}$ are each independently (C1-C10)alkyl or halo(C1-C10)alkyl;

q and r are each independently an integer of 0 to 2; and p1 and m1 are each independently an integer of 0 to 3.

Specifically, in Chemical Formula 1-12, $D^1$ may be (C1-C10)alkylene substituted or unsubstituted with halo(C1-C5)alkyl; $R^{21}$ and $R^{22}$ may be each independently halogen, C1-C10 alkyl, or halo C1-C10 alkyl; $R^{23}$ may be hydrogen or (C1-C10)alkyl; $R^{27}$ and $R^{28}$ may be each independently (C1-C5)alkyl or halo(C1-C5)alkyl; and q, r, p1, and m1 may be each independently an integer of 0 or 1.

The polyimide film according to an exemplary embodiment of the present invention may essentially have the repeating unit represented by Chemical Formula 1-9 and may further have the repeating unit represented by Chemical Formula 1-10. specifically, the polyimide film may essentially have the repeating unit represented by Chemical Formula 1-9 and may further have the repeating unit represented by Chemical Formula 1-11 and the repeating unit represented by Chemical Formula 1-12. More specifically, the polyimide film may essentially have the repeating unit represented by Chemical Formula 1-9 and may further have the repeating unit represented by Chemical Formula 1-10 and the repeating unit represented by Chemical Formula 1-11. Still more specifically, the polyimide film may essentially have the repeating unit represented by Chemical Formula 1-9, and may further have the repeating unit represented by Chemical Formula 1-10, the repeating unit represented by Chemical Formula 1-11, and the repeating unit represented by Chemical Formula 1-12.

The polyimide film according to an exemplary embodiment of the present invention may have a low coefficient of thermal expansion and a low yellow index, may prevent warpage or curve, and may have excellent transparency and an excellent Young's modulus.

The coefficient of thermal expansion (CTE) of the polyimide film according to an exemplary embodiment of the present invention may be 20 ppm/° C. or less, specifically 15 ppm/° C. or less, more specifically 10 ppm/° C. or less, still more specifically more than 0 to 20 ppm/° C., still more specifically more than 0 to 15 ppm/° C., and particularly specifically more than 0 to 12 ppm/° C., at 100° C. to 450° C.

The yellow index (YI) of the polyimide film according to an exemplary embodiment of the present invention when measured according to ASTM E313 may be less than 25, specifically 20 or less, more specifically 16 or less, still more specifically 1 to less than 25, still more specifically 3 to 20, and particularly Specifically 3 to 16.

The Young's modulus of the polyimide film according to an exemplary embodiment of the present invention when measured according to ASTM D882 may be 6.0 or more, specifically more than 6.5, more specifically more than 6.0 to 8.5, and still more specifically more than 6.5 to less than 8.0.

Specifically, the coefficient of thermal expansion of the polyimide film according to an exemplary embodiment of the present invention may be 20 ppm/° C. or less at 100° C. to 450° C., the YI of the polyimide film when measured according to ASTM E313 may be less than 25, and the Young's modulus of the polyimide film when measured according to ASTM D882 may be more than 6.0. More specifically, the coefficient of thermal expansion of the polyimide film may be 15 ppm/° C. or less at 100° C. to 450° C., the YI of the polyimide film when measured according to ASTM E313 may be 20 or less, and the Young's modulus of the polyimide film when measured according to ASTM D882 may be more than 6.8. Still more specifically, the coefficient of thermal expansion of the polyimide film may be 12 ppm/° C. or less at 100° C. to 450° C., the YI of the polyimide film when measured according to ASTM E313 may be 16 or less, and the Young's modulus of the polyimide film when measured according to ASTM D882 may be more than 6.0.

Specifically, the coefficient of thermal expansion of the polyimide film according to an exemplary embodiment of the present invention may be more than 0 to 20 ppm/° C. at 100° C. to 450° C., the YI of the polyimide film when measured according to ASTM E313 may be 1 to 25, and the Young's modulus of the polyimide film when measured according to ASTM D882 may be more than 6.0 to 8.5. More specifically, the coefficient of thermal expansion of the polyimide film may be more than 0 to 15 ppm/° C. or less at 100° C. to 450° C., the YI of the polyimide film when measured according to ASTM E313 may be 3 to 20, and the Young's modulus of the polyimide film when measured according to ASTM D882 may be more than 6.5 to 8.5. Still more specifically, the coefficient of thermal expansion of the polyimide film may be more than 0 to 12 ppm/° C. at 100° C. to 450° C., the YI of the polyimide film when measured according to ASTM E313 may be 3 to 16, and the Young's modulus of the polyimide film when measured according to ASTM D882 may be more than 6.5 to less than 8.0.

A total light transmittance of the polyimide film of the present invention may be 80% or more and specifically 85% or more.

The polyimide film according to an exemplary embodiment of the present invention is produced using the diamine compound of the present invention into which $CF_3$ that is a specific functional group is introduced at a specific backbone and a specific position, such that the polyimide film has excellent optical and mechanical properties.

Specifically, the polyimide film has the repeating unit derived from the diamine compound represented by Chemical Formula 1 according to an exemplary embodiment of the present invention, such that the polyimide film may have excellent optical properties, heat resistance, mechanical strength, and flexibility. Therefore, the polyimide film of the present invention may be used in various fields such as a substrate for a device, a cover substrate for a display device, an optical film, an integrated circuit (IC) package, an adhesive film, a multi-layer flexible printed circuit (FRC), a tape, a touch panel, and a protective film for an optical disk.

A weight average molecular weight of the polyimide film according to an exemplary embodiment of the present invention, that is, the polyimide, may be 10,000 to 200,000 g/mol, 20,000 to 100,000 g/mol, or 30,000 to 100,000 g/mol. In addition, a molecular weight distribution (Mw/Mn) of the polyimide according to the present invention may be in a range of 1.1 to 2.5. When the weight average molecular weight and the molecular weight distribution of the polyimide are in the above ranges, the polyimide film may have excellent properties such as optical properties, heat resistance, mechanical strength, and flexibility.

A thickness of the polyimide film according to an exemplary embodiment of the present invention may be 5 to 15 μm.

The polyimide film according to an exemplary embodiment of the present invention may have excellent heat resistance according to a temperature change. Specifically, in a case where a change in thermal expansion when a first heating process is performed at a heating rate of 5° C./min in a temperature range of 100° C. to 450° C. and then cooling is performed at a cooling rate of 4° C./min in a temperature range of 400° C. to 100° C. is measured with a TMA (TMA 450, TA Instruments) in the above thickness range, the coefficient of thermal expansion (CTE) of the polyimide film may be 20 ppm/° C. or less. The coefficient of thermal expansion (CTE) may be, specifically, 15 ppm/° C. or less, and more specifically, −20 to 10 ppm/° C.

The polyimide film according to an exemplary embodiment of the present invention may have excellent optical properties, heat resistance, mechanical strength, and flexibility due to a rigid structure derived from the diamine compound represented by Chemical Formula 1. In particular, the polyimide film may have excellent heat resistance against thermal shrinkage behavior that may occur during a high-temperature process and excellent colorless and transparent optical properties. Therefore, the polyimide film may be used in various fields such as a substrate for a device, a substrate for a display device, an optical film, an integrated circuit (IC) package, an adhesive film, a multi-layer flexible printed circuit (FRC), a tape, a touch panel, and a protective film for an optical disk.

The polyimide film according to an exemplary embodiment of the present invention may be used as a laminate in which two or more layers are laminated.

In addition, the present invention provides a photoelectric device and a flexible display device that include the polyimide film or a laminate in which the polyimide films are laminated as a flexible substrate.

Examples of the photoelectric device may include an optical component, a switch, and an optical modulator, and the photoelectric device is suitable for a high heat resistant substrate material requiring fine pattern formation characteristics.

Examples of the flexible display device may include a liquid crystal display (LCD) device and an organic light emitting diode (OLED) device, and the flexible display device is suitable for an OLED device obtained by using a low temperature polysilicon (LIPS) process requiring a high-temperature process, but is not limited thereto.

Hereinafter, the present invention will be described with reference to specific Examples and Comparative Examples. The following Examples are illustrative only to describe the technical idea of the present invention, and those skilled in the art will appreciate that the present invention is not limited to Examples.

[Evaluation Methods]

1. Coefficient of Thermal Expansion (CTE) and Glass Transition Temperature (Tg)

A coefficient of thermal expansion (CTE) was measured according to a TMA-method using a TMA (Discovery 450, TA Instruments). A size of a sample was set to 5 mm×20 mm, a load was set to 0.02N, and a heating rate was set to 5° C./min. A CTE value was measured in a heating section of a temperature range of 100° C. to 450° C.

A Tg value was measured in a heating section of 100° C. to 450° C. at an inflection point of a TMA graph.

2. Yellow Index (YI)

A yellow index (YI) of a polyimide film having a thickness of 10 μm was measured according to ASTM E313 using a colorimeter (ColorQuest XE, Hunter Associates Laboratory, Inc.).

3. Total Light Transmittance

A total light transmittance of a polyimide film having a thickness of 10 μm was measured in the entire wavelength range of 380 to 780 nm according to ASTM D1746 using a spectrophotometer (MPC-3100, Shimadzu Corporation). A unit of the total light transmittance is %

4. Young's Modulus

A Young's modulus of a polyimide film having a thickness of 10 μm, a length of 40 mm, and a width of 5 mm was measured under a condition in which the polyimide film was pulled at 25° C. and 10 mm/min according to ASTM D882 using a UTM 3365 (Instron Corporation). A unit of the modulus is GPa.

5. Thickness

A thickness of a substrate obtained by coating PAA to 0.5 T glass and performing curing was measured using a film thickness gauge (Alpha step D500, KLA Corporation). A unit of the thickness is μm.

6. Viscosity

A viscosity means a value measured by placing a sample at room temperature (25° C.) using a Brookfield RVDV-III viscometer spindle No. 52 and stabilizing the sample for 2 minutes at the time when a torque value reaches 80%. A unit of the viscosity is cps.

7. Weight Average Molecular Weight

A weight average molecular weight was measured by dissolving a film in a DMAc eluent containing 0.05 M LiBr. A Waters GPC system, a Waters 1515 isocratic HPLC Pump, a Waters 2414 Refractive Index detector were used as GPC, an Olexis, a Polypore, and a mixed D column were connected to each other and used as a column, polymethyl methacrylate (PMMA STD) was used as a standard material, and the analysis was performed at 35° C. and a flow rate of 1 mL/min.

[Preparation Example 1] Preparation of Diamine Compound 1

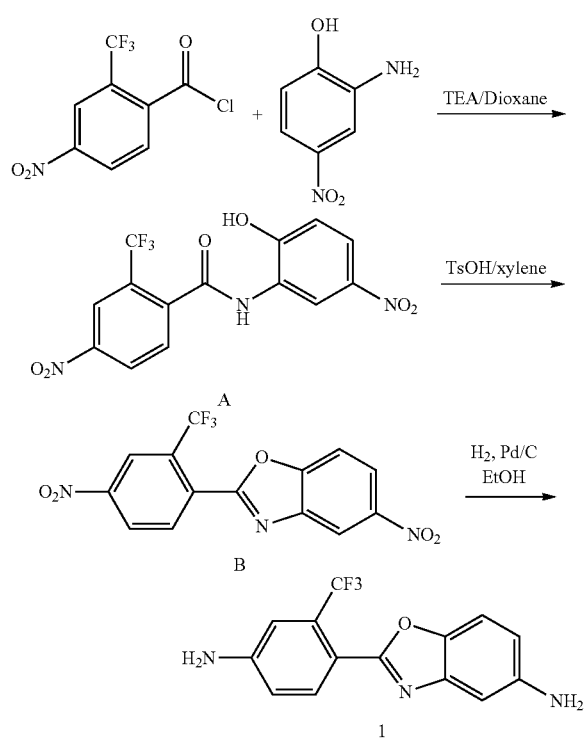

Step 1. Preparation of Compound A

Under a nitrogen atmosphere, 1 L of DCM was added to 4-nitro-2-trifluoromethyl benzoic acid (60 g) and cooling was performed to 0° C. Oxalic chloride (47 g) was slowly added, a reaction was allowed to proceed for 1 hour, and then, 2 g of N,N-dimethylformamide (DMF) was added. Stirring was performed at room temperature for 6 hours, and a solvent was removed by vacuum distillation, thereby obtaining 64 g of 4-nitro-2-trifluoromethyl benzoylchloride. 39 g of 2-amino-4-nitrophenol and 7 g of TEA were dissolved in 390 mL of dioxane in an additional reactor, and cooling was performed to 0° C. 64 g of the prepared benzoylchloride was dissolved in 250 mL of dioxane and slowly added. The temperature was increased to room temperature, stirring was performed for 12 hours, and a solvent was removed by vacuum distillation. The obtained solid was washed with 1 N HCl, and filtering was performed, thereby obtaining 72 g of a yellow solid compound A (2-trifluoromethyl-N-(2-hydroxyl-5-nitrophenyl)-4-nitrobenzamide) (yield: 76%).

Step 2. Preparation of Compound B 72 g of 4-methylbenzenesulfonic acid and 750 mL of xylene were added to the compound A (benzamide) prepared in step 1, and reflux was performed for 6 hours. A solvent was removed by vacuum distillation, and EtOH and H$_2$O were precipitated in a ratio of 1:1 (EtOH/H$_2$O), thereby obtaining 51 g of a compound B (5,4'-dinitro-2'-trifluoromethyl-2-phenylbenzoxazole) (yield: 74%).

Step 3. Preparation of Diamine Compound 1

The compound B obtained in step 2 was dissolved in 500 mL of EtOH, and 5 g of 10% PdC was added. Stirring was performed while bubbling H$_2$ for 6 hours, filtering was performed, and then a catalyst was removed and a solvent was removed by vacuum distillation. The residue was recrystallized with EtOH to obtain 33 g of a light brown diamine compound 1 (5,4'-diamino-2'-trifluoromethyl-2-phenylbenzoxazole) (yield: 78%).

$^1$H NMR (DMSO-d$_6$, 500 MHz, ppm): 7.82 (d, 1H, J=8.5 Hz), 7.33 (d, 1H, J=8.5 Hz), 7.06 (d, 1H, J=2 Hz), 6.882 (d, 1H, J=8.5 Hz), 6.82 (d, 1H, J=2 Hz), 6.63 (dd, 1H, J=8.5, 2 Hz), 6.24 (s, NH$_2$), 5.04 (Br, NH$_2$).

[Preparation Example 2] Preparation of Diamine Compound 2

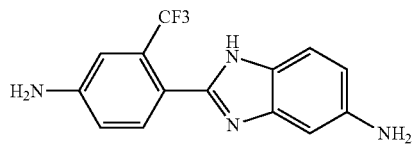

A diamine compound 2 was prepared as described in Polymer 49 (2008) 2644-2649.

[Example 1] Preparation of Polyimide Precursor Solution

PMDA/compound 1 (molar ratio: 1/0.999)

A stirrer was filled with 184 g of N,N-dimethylpropionamide (DMPA) under a nitrogen atmosphere, and 20.13 g of the diamine compound (compound 1) was dissolved while the temperature of the reactor was maintained at 25° C. 15.00 g of pyromellitic dianhydride (PMDA) was added to the diamine compound 1 solution at the same temperature, and stirring was performed while dissolving PMDA for a certain period of time. DMPA was added so that a solid content concentration of the polyimide precursor solution prepared by the above reaction was 10.5 wt % to prepare a polyimide precursor solution. A viscosity of the polyimide precursor solution was 4,100 cps. A molecular weight Mw of the solution was 91,000 g/mol.

Example 2

6FDA/PMDA/compound 1/TFMB (molar ratio: 0.3/0.7/0.5/0.5)

A stirrer was filled with 203 g of N,N-dimethylpropionamide (DMPA) under a nitrogen atmosphere, and 10.48 g of 2,2'-bis(trifluoromethyl)-4,4'-biphenyl diamine (TFMB) and 9.59 g of the compound 1 were dissolved while the temperature of the reactor was maintained at 25° C. 8.72 g of 4,4'-(hexafluoroisopropylidene)diphthalic anhydride (6FDA) and g of pyromellitic dianhydride (PMDA) were added to the TFMB/compound 1 solution at the same temperature, and stirring was performed while dissolving 6FDA and PMDA for a certain period of time. DMPA was added so that a solid content concentration of the polyimide precursor solution prepared by the above reaction was 10.4 wt % to prepare a polyimide precursor solution. A viscosity of the polyimide precursor solution was 4,500 cps. A molecular weight Mw of the solution was 95,000 g/mol.

Example 3

6FDA/PMDA/compound 2/compound 1 (molar ratio: 0.3/ 0.7/0.5/0.5)

A stirrer was filled with 218.5 g of N,N-dimethylpropionamide (DMPA) under a nitrogen atmosphere, and 10.3 g of the compound 2 and 10.33 g of the compound 1 were dissolved while the temperature of the reactor was maintained at 25° C. 10.96 g of 4,4'-(hexafluoroisopropylidene) diphthalic anhydride (6FDA) and 10 g of pyromellitic dianhydride (PMDA) were added to the compound 2/compound 1 solution at the same temperature, and stirring was performed while dissolving 6FDA and PMDA for a certain period of time. A viscosity of the polyimide precursor solution was 4,300 cps. A molecular weight Mw of the solution was 89,000 g/mol.

Comparative Example 1

PMDA/2,5-diaminobenzoxazole (molar ratio: 1/0.999)

A stirrer was filled with 161 g of N,N-dimethylpropionamide (DMPA) under a nitrogen atmosphere, and 15.66 g of 2,5-diaminobenzoxazole was dissolved while the temperature of the reactor was maintained at 25° C. 15 g of pyromellitic dianhydride (PMDA) was added to the 2,5-diaminobenzoxazole solution at the same temperature, and stirring was performed while dissolving PMDA for a certain period of time. DMPA was added so that a solid content concentration of the polyimide precursor solution prepared by the above reaction was 9.3 wt % to prepare a polyimide precursor solution. A viscosity of the polyimide precursor solution was 4,800 cps. A molecular weight Mw of the solution was 93,000 g/mol.

Comparative Example 2

PMDA/1H-benzimidazole-2,5-diamine (molar ratio: 1/0.999)

A stirrer was filled with 159 g of N,N-dimethylpropionamide (DMPA) under a nitrogen atmosphere, and 15.40 g of 1H-benzimidazole-2,5-diamine was dissolved while the temperature of the reactor was maintained at 25° C. 15 g of pyromellitic dianhydride (PMDA) was added to the 1H-benzimidazole-2,5-diamine solution at the same temperature, and stirring was performed while dissolving PMDA for a certain period of time. DMPA was added so that a solid content concentration of the polyimide precursor solution prepared by the above reaction was 9.1 wt % to prepare a polyimide precursor solution. A viscosity of the polyimide precursor solution was 5,100 cps. A molecular weight Mw of the solution was 105,000 g/mol.

Comparative Example 3

PMDA/compound 2 (molar ratio: 1/0.999)

A stirrer was filled with 184.2 g of N,N-dimethylpropionamide (DMPA) under a nitrogen atmosphere, and 20.07 g of the diamine compound (compound 2) was dissolved while the temperature of the reactor was maintained at 25° C. 15 g of pyromellitic dianhydride (PMDA) was added to the solution at the same temperature, and stirring was performed while dissolving PMDA for a certain period of time. DMPA was added so that a solid content concentration of the polyimide precursor solution prepared by the above reaction was 10.4 wt % to prepare a polyimide precursor solution. A viscosity of the polyimide precursor solution was 4,300 cps. A molecular weight Mw of the solution was 95,000 g/mol.

Comparative Example 4

6FDA/PMDA/compound 2/TFMB (molar ratio: 0.3/0.7/ 0.5/0.5)

A stirrer was filled with 203 g of N,N-dimethylpropionamide (DMPA) under a nitrogen atmosphere, and 10.48 g of 2,2'-bis(trifluoromethyl)-4,4'-biphenyl diamine (TFMB) and 9.57 g of the compound 2 were dissolved while the temperature of the reactor was maintained at 25° C. 8.72 g of 4,4'-(hexafluoroisopropylidene)diphthalic anhydride (6FDA) and g of pyromellitic dianhydride (PMDA) were added to the TFMB/compound 2 solution at the same temperature, and stirring was performed while dissolving 6FDA and PMDA for a certain period of time. DMPA was added so that a solid content concentration of the polyimide precursor solution prepared by the above reaction was 10.6 wt % to prepare a polyimide precursor solution. A viscosity of the polyimide precursor solution was 4,600 cps. A molecular weight Mw of the solution was 93,000 g/mol.

[Example 4] Production of Polyimide Film

The polyimide precursor solution prepared in each of Examples 1 to 3 and Comparative Examples 1 to 4 was spin-coated onto a glass substrate at a thickness of 10 μm. The glass substrate onto which the polyimide precursor solution was coated was placed into an oven to heat the glass substrate at a rate of 4° C./min, and a curing process was performed while maintaining the glass substrate at 80° C. for 30 minutes, 220° C. for 30 minutes, and 450° C. for 1 hour. After completing the curing process, the glass substrate was immersed in water to detach a film formed on the glass substrate, and the film was dried in an oven at 100° C., thereby producing a polyimide film.

The physical properties of the polyimide film produced by the above method were measured by the above evaluation methods. The results are shown in Table 1.

TABLE 1

|  | Unit | Example 1 | Example 2 | Example 3 | Comparative Example 1 | Comparative Example 2 | Comparative Example 3 | Comparative Example 4 |
| --- | --- | --- | --- | --- | --- | --- | --- | --- |
| Thickness | um | 10 | 10 | 10 | 10 | 10 | 10 | 10 |
| Sol. Con. | wt % | 10.5 | 10.4 | 10.2 | 9.3 | 9.1 | 10.3 | 10.6 |
| Viscosity | cps | 4,100 | 4,300 | 4,700 | 4,500 | 5,100 | 4,500 | 4,600 |
| Tg | ° C. | N. D. | N.D. | N.D. | N.D. | N.D. | N.D. | N.D. |

TABLE 1-continued

| | Unit | Example 1 | Example 2 | Example 3 | Comparative Example 1 | Comparative Example 2 | Comparative Example 3 | Comparative Example 4 |
|---|---|---|---|---|---|---|---|---|
| CTE 100° C. to 450° C. | ppm/° C. | 7.5 | 11.3 | 5.7 | −11 | −9.5 | −17 | 15.5 |
| Total light transmittance (380 to 780 nm) | % | 85 | 88 | 87 | 87 | 76 | 85 | 88 |
| Yellow index (YI) | — | 7.5 | 12.5 | 15.3 | 25 | 42 | 23 | 11.6 |
| Young's modulus | GPa | 6.8 | 7.8 | 7.3 | 7.3 | 7.9 | 8.0 | 7.8 |

As shown in Table 1, it can be appreciated that the polyimide film produced using the polyimide precursor solution derived from the diamine compound of the present invention in each of Examples 1 to 3 has uniformly improved physical properties such as the coefficient of thermal expansion, the total light transmittance, the yellow index, and the Young's modulus as compared to those in each of Comparative Examples 1 to 4.

In particular, in the case of the polyimide film of Example 3 produced using the polyimide precursor solution having the structural unit derived from the diamine compound of the present invention and further having the structural unit derived from the diamine compound represented by Chemical Formula 4 of the present invention, the polyimide film is produced using the polyimide precursor solution prepared by combining the diamine compound whose value of the coefficient of thermal expansion is negative with the diamine compound whose value of the coefficient of thermal expansion is positive, such that the value of the coefficient of thermal expansion is very close to 0. Therefore, a low temperature polysilicon TFT (LTPS TFT) may be subjected to a high-temperature process.

As a result, a polyimide film having high heat resistance and excellent optical and mechanical properties such as a coefficient of thermal expansion, a yellow index, and a Young's modulus may be produced by using the polyimide precursor solution of the present invention.

As set forth above, the novel diamine compound of the present invention may have a specific backbone and substituent, such that the polyimide film produced using the diamine compound may have a significantly improved coefficient of thermal expansion, transparency, and heat resistance and an excellent yellow index, breaking strength, and Young's modulus.

Further, in the polyimide film produced using the novel diamine compound of the present invention as a monomer, the coefficient of thermal expansion and the residual stress may be excellent because a stress of a substrate does not increase even after performing a heat treatment at a high temperature, and thus, the problems such as warpage, peeling, and fracture do not occur.

Therefore, the polyimide film produced using the composition containing the novel diamine compound of the present invention may have excellent optical properties due to a reduction of optical anisotropy and may implement a uniform transmittance and excellent transparency.

Further, the polyimide film produced using the composition containing the diamine compound of the present invention may be colorless and transparent and may have excellent heat resistance, mechanical strength, and flexibility. Therefore, the polyimide film may be very usefully used in various fields such as a substrate for a device, a substrate for a flexible display device, an optical film, an integrated circuit (IC) package, an adhesive film, a multi-layer flexible printed circuit (FPC), a tape, a touch panel, and a protective film for an optical disk.

Hereinabove, although the present invention has been described by specific matters and limited exemplary embodiments, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to these exemplary embodiments, but the claims and all modifications equal or equivalent to the claims are intended to fall within the scope and spirit of the present invention.

What is claimed is:

1. A diamine compound represented by the following Chemical Formula 2,

[Chemical Formula 2]

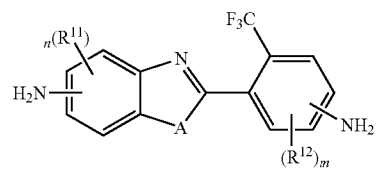

wherein in Chemical Formula 2,

A is O or S;

$R^{11}$ and $R^{12}$ are each independently halogen, C1-C10 alkyl, halo C1-C10 alkyl, C1-C10 alkoxy, or C6-C12 aryl; and n and m are each independently an integer of 0 to 2.

2. The diamine compound of claim 1, wherein in Chemical Formula 2,

A is O;

$R^{11}$ and $R^{12}$ are each independently halogen, C1-C10 alkyl, or halo C1-C10 alkyl; and n and m are each independently an integer of 0 or 1.

3. The diamine compound of claim 2, wherein in Chemical Formula 2,

A is O;

$R^{11}$ and $R^{12}$ are each independently halogen, C1-C5 alkyl, or halo C1-C5 alkyl; and n and m are each independently an integer of 0 or 1.

4. The diamine compound of claim 1, wherein the diamine compound is selected from the following compounds,

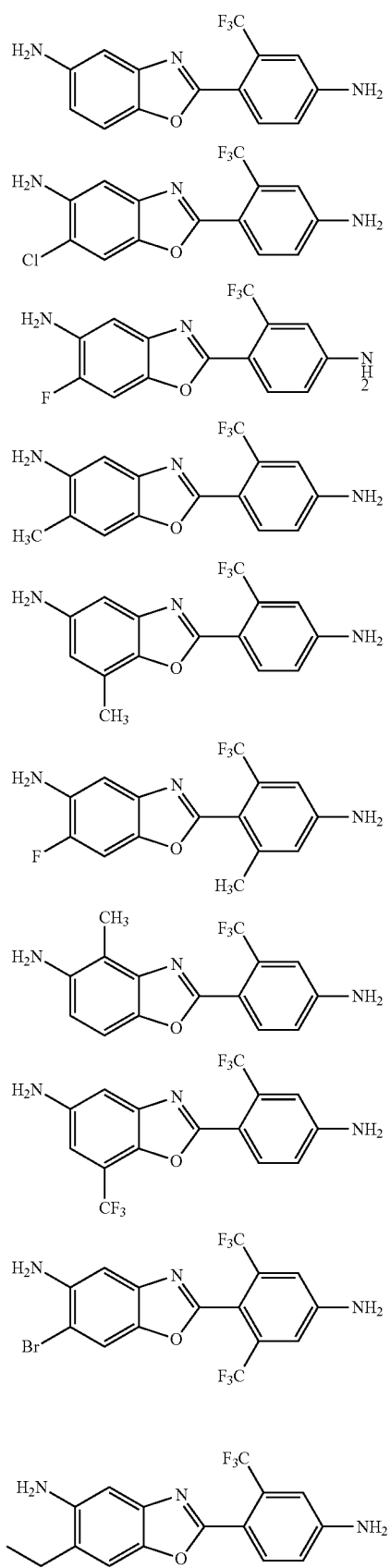
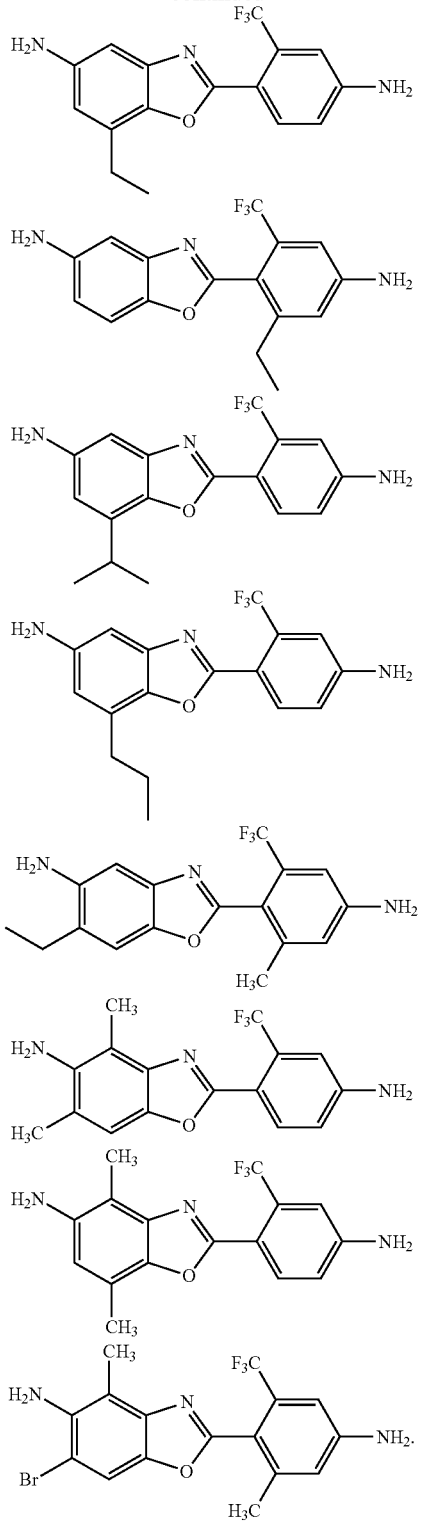
5. A composition comprising the diamine compound of claim 1.
6. The composition of claim 5, wherein the diamine compound is contained in an amount of 1 to 30 wt % with respect to a total weight of the composition.
* * * * *